US006740631B2

(12) United States Patent
Shefer et al.

(10) Patent No.: US 6,740,631 B2
(45) Date of Patent: May 25, 2004

(54) MULTI COMPONENT CONTROLLED DELIVERY SYSTEM FOR FABRIC CARE PRODUCTS

(76) Inventors: Adi Shefer, 14 Jason Dr., East Brunswick, NJ (US) 08816; Samuel David Shefer, 14 Jason Dr., East Brunswick, NJ (US) 08816

(*) Notice: Subject to any disclaimer, the term of this patent is extended or adjusted under 35 U.S.C. 154(b) by 17 days.

(21) Appl. No.: 10/133,833

(22) Filed: Apr. 26, 2002

(65) Prior Publication Data

US 2003/0203829 A1 Oct. 30, 2003

(51) Int. Cl.$^7$ .................................................. A61K 9/51

(52) U.S. Cl. ........................... 510/441; 510/101; 512/4; 424/451; 424/458; 424/485; 424/486

(58) Field of Search ................................ 424/450, 451, 424/457, 458, 469, 486, 485; 510/441, 515, 101, 438; 512/4

(56) References Cited

U.S. PATENT DOCUMENTS

| | | | | |
|---|---|---|---|---|
| 4,152,272 | A | | 5/1979 | Young |
| 4,402,856 | A | | 9/1983 | Schnoring et al. |
| 4,446,032 | A | | 5/1984 | Munteanu et al. |
| 4,464,271 | A | | 8/1984 | Munteanu et al. |
| 4,919,841 | A | | 4/1990 | Kamel et al. |
| 4,946,624 | A | | 8/1990 | Michael |
| 4,954,285 | A | | 9/1990 | Wierenga et al. |
| 4,973,422 | A | | 11/1990 | Schmidt |
| 5,066,419 | A | | 11/1991 | Walley et al. |
| 5,094,761 | A | | 3/1992 | Trinh et al. |
| 5,102,564 | A | | 4/1992 | Gardlik et al. |
| 5,112,688 | A | | 5/1992 | Michael |
| 5,126,061 | A | | 6/1992 | Michael |
| 5,137,646 | A | | 8/1992 | Schmidt et al. |
| 5,154,842 | A | | 10/1992 | Walley et al. |
| 5,207,933 | A | | 5/1993 | Trinh et al. |
| 5,232,612 | A | | 8/1993 | Trinh et al. |
| 5,234,610 | A | | 8/1993 | Gardlik et al. |
| 5,234,611 | A | | 8/1993 | Trinh et al. |
| 5,236,615 | A | | 8/1993 | Trinh et al. |
| 5,246,603 | A | | 9/1993 | Tsaur et al. |
| 5,425,887 | A | | 6/1995 | Lam et al. |
| 5,476,660 | A | | 12/1995 | Somasundaran et al. |
| 6,024,943 | A | | 2/2000 | Ness et al. |
| 6,042,792 | A | | 3/2000 | Shefer et al. |
| 6,051,540 | A | | 4/2000 | Shefer et al. |
| 6,083,899 | A | | 7/2000 | Baker et al. |
| 6,395,302 | B1 | * | 5/2002 | Hennink et al. ............ 424/489 |
| 6,500,446 | B1 | * | 12/2002 | Derrieu et al. .............. 424/408 |

* cited by examiner

*Primary Examiner*—John Hardee
(74) *Attorney, Agent, or Firm*—Mathews, Collins, Shepherd & McKay, P.A.

(57) ABSTRACT

The present invention relates to an improved controlled delivery system that can be incorporated in dry granular, or powder, fabric care products, such as laundry detergents, tumble dryer sheets, rinse added products, and other fabric care products, to enhance fragrance performance. The controlled delivery system of the present invention comprises substantially free-flowing, powder formed of solid hydrophobic, positively charged, nano-spheres of encapsulated active ingredients, such as a fragrance, that are encapsulated in a moisture sensitive micro-spheres, solid spheres. The high cationic charge density of the nano-sphere improves fragrance deposition onto the laundered fabric. The high cationic charge density on the nano-sphere surface is created by incorporating a cationic fabric conditioning agent into the solid hydrophobic matrix of the nano-spheres, by incorporating a cationic charge "booster" in the water sensitive micro-sphere matrix, or by using a cationic fabric conditioning agent in the nano-sphere matrix in conjunction with a cationic charge "booster" in the micro-sphere matrix. The fragrance carrier system also provides controlled release or prolonged fragrance release from the dry laundered fabric over an extended period of time, or yields a high impact fragrance "burst" upon ironing the fabric. The invention also pertains to fabric care products comprising the controlled release system of the present invention.

42 Claims, 1 Drawing Sheet

MULTI COMPONENT CONTROLLED DELIVERY SYSTEM FOR FABRIC CARE PRODUCTS

BACKGROUND OF THE INVENTION

1. Field of the Invention

The present invention relates to an improved controlled release carrier system that can be incorporated into fabric care products, such as fabric softener, laundry detergents, tumble dryer sheets, and other fabric care products, that enhances deposition of active ingredients as well as fragrances onto fabric and which provides prolong release of active ingredients and fragrances from the dry laundered fabric over an extended period of time, or yields a high impact fragrance "burst" upon ironing the fabric.

2. Description of the Related Art

The household industry has searched for many years for ways to enhance the performance of fabric care products and make them more aesthetically pleasing for the consumers. Consumer acceptance of laundry products is determined not only by the performance achieved with these products but the aesthetics associated therewith. Fragrance is an important aspect of the successful fabric care products and they are being utilized, in addition to imparting an aesthetically pleasing odor, to convey to the consumer the product performance and effectiveness (i.e., the fabric is clean, freshly washed, etc.).

Fragrances are typically added to fabric care products to provide a fresh, clean impression for these products as well as the laundered fabric. While the fragrance does not add to the performance of fabric care products, it does make these products more aesthetically pleasing and the consumer has come to expect such products to have a pleasing odor. The fragrance plays a major, and often determining, role for the consumer in selecting and purchasing the fabric care product. Consumers are becoming increasingly educated and expect a high level of sophistication in their fabric care products. Many consumers would prefer for the fragrance present in these products, to be deposited on the fabric and remain there for an extended period of time to convey a lasting impression of freshness. Consumers are also interested in fabric care products that deposit high level of fragrance onto the fabric and release the fragrance upon ironing. Fragrance creation for fabric care products is restricted not only by considerations such as availability and cost, but also by compatibility of the fragrance ingredients to deposit onto the fabric and survive the wash and rise process. Furthermore, large amount of fragrance is being lost during the drying process, even when the fabrics are line dried. Practice has shown that when currently available fabric care products are used, a large fraction of the fragrance is lost during the rinse process due to the solubility of certain fragrance ingredients in aqueous washing compositions, and the fraction of the fragrance which was deposited, quickly evaporates, due to the volatility of fragrance ingredients.

Typical fabric care products such as laundry detergent compositions and fabric softener compositions contain 0.5% to 1% by weight fragrance in their formulations. U.S. Pat. No. 6,051,540, issued to the inventor of this disclosure, disclosure, discloses that in the course of the washing process wherein clothes are washed with the standard powdered laundry detergent, or fabric softener rinse, a very small fraction of the fragrance that is contained in these fabric care products is actually transferred to the clothes. Tests are described showing that the amount of fragrance that is left as a residue on the clothes can be as low as 1% of the original small amount of fragrance that is contained in these products formulation itself.

Attempts have been made to increase fragrance deposition onto fabric and to hinder or delay the release of the perfume so that the laundered fabric remains aeshtetically pleasing for a prolonged length of time. One approach used a carrier to bring the fragrance to the clothes. The carrier is formulated to contain a fragrance and to attach itself to the clothes during the washing cycle through particle entrainment or chemical change.

Perfumes have been adsorbed onto various materials such as silica and clay to deliver perfume in detergents and fabric softeners. U.S. Pat. No. 4,954,285 discloses perfume particles especially for use in dryer released fabric softening/antistatic agents. The perfume particles are formed, by adsorbing the perfume onto silica. The particles have a diameter of greater than about one micron. The particles can be used to reduce the shiny appearance of visible softener spots, which occasionally are present on fabrics treated with said fabric softening compositions and to maintain a relatively constant viscosity of the molten softening composition. The perfume particles are especially adapted for inclusion in dryer activated solid fabric softener compositions including coated particles of fabric softener, which are added to a detergent composition for use in the washing of fabrics. The compositions release softener to the fabrics in the dryer and improve the aesthetic character of any fabric softener deposits on fabrics. The perfume particles can also be admixed with detergent granules and can either be coated or uncoated. This system has the drawback that the fragrance oil is not sufficiently protected and is frequently lost or destabilized during processing.

U.S. Pat. Nos. 4,946,624, 5,112,688, and 5,126,061 disclose microcapsules, prepared by a coacervation process. The microcapsules have a complex structure in which there is a large central core of encapsulated material, preferably perfume, and the walls contain small wall inclusion particles of either the core material or some other material that can be activated to disrupt the wall. The microcapsules that are prepared by coacervation and contain perfume are incorporated into fabric softener compositions that have a pH of about 7 or less and which contain cationic fabric softener. The encapsulated perfume preferably does not contain large amounts of relatively water-soluble ingredients. Such ingredients are added separately to the fabric softener compositions. Ingredients that have high and low volatilities as compared to desired perfume, can either be added to, or removed from, the perfume to achieve the desired volatility. These type of controlled release system have the limitation of not working with all type of fragrance ingredients, especially not with fragrance ingredients that are relatively water-soluble and do not deposit into the fabric.

U.S. Pat. No. 4,402,856 describes the use of coacervation technique to create perfume particles for fabric care products composed of gelatin or a mixture of gelatin with gum arabic, carboxymethylcellulose and/or anionic polymers. The gelatin is hardened with a natural and/or synthetic tanning agent and with a carbonyl compound. According to the invention, the particles adhere to the fabric and are carried over to the dryer. Diffusion of the perfume out of the capsules occurs only in heat-elevated conditions of the dryer.

U.S. Pat. No. 4,152,272 teaches incorporating perfume into wax particles to protect the perfume during storage and through the laundry process. The perfume/wax particles are incorporated into an aqueous fabric conditioner composition. The perfume then diffuses from the particles onto the fabric in the heat-elevated conditions of the dryer.

U.S. Pat. No. 4,919,841 discloses wax encapsulated actives based on emulsion process for household applications including fabric. The process for preparing encapsulated active particles comprises the steps of: dispersing active materials in molten wax; emulsifying the active/wax dispersion in aqueous surfactant solution; quenching the capsules by cooling; and retrieving solidified capsules. The active materials may be selected from chlorine or oxygen bleaching agents, bleach precursors, enzymes, perfumes, fabric softening agents, and surfactants. The resultant capsules are in a form of dispersion (liquid) and have utility for cleaning compositions such as automatic dishwashing detergent formulations.

U.S. Pat. No. 5,246,603 describes composite microcapsules that are incorporated into a tumble drier article. The microcapsules comprise particles made of mixture of a wax material and a fragrance oil which are embedded in a water soluble polymer. The microcapsules have a diameter of less than about 100 microns and are useful for incorporation in tumble drier articles to control the release of fragrance in the drier and prevent loss of fragrance during processing and storage U.S. Pat. No. 5,425,887 describes perfume capsules consisting of a water soluble natural or modified natural or synthetic polymer and perfume for a tumble dryer article. The perfume capsules are formed by mixing the polymer and the water to form a solution, adding the perfume to the solution to form an emulsified mixture and either spray drying or coacervating the emulsified mixture.

U.S. Pat. No. 6,042,792 issued to the inventor of this disclosure also describes an aqueous dispersion. A controlled, time-release microparticulate active and bioactive compositions (including perfuming compositions) for targeted delivery to services such as skin, hair and fabric and the environment proximate thereto is described in which the active and bioactive materials have a calculated log P values of between 1 and 8 (P being the n-octanol-water partition coefficient). Such compositions include the active or bioactive material in single phase, solid solution in a wax or polymer matrix also having coated thereon and/or containing a compatible surfactant. Also described are processes and apparatus for preparing such compositions and processes for using same. The fragrance formulation is selected and according this patent has the disadvantage of limiting the type of fragrances that can be used with the system.

U.S. Pat. Nos. 4,446,032 and 4,464,271 disclose liquid or solid fabric softener compositions comprising microencapsulated fragrance suspensions. The compositions contain sustained release fragrances that are prepared by combining non-confined fragrance Oils with encapsulated or physically entrapped fragrance oils. These combinations are fashioned so that the free fragrance oil or fragrance oil emulsion, are bound in a network of physically entrapped fragrance oil and suspending agent. The thixatropic pastes or free-flowing powders which result are products where the unconfined fragrance oil or unconfined fragrance oil emulsion, the "encapsulated" or physically entrapped fragrance oil and suspending agent are held together by physical forces. The controlled release system comprise of a mixture of (i) a non-confined fragrance composition; (ii) one or more fragrance oils which are physically entrapped in one or more types of solid particles and (iii) a suspending agent such as hydroxypropyl cellulose, silica, xanthan gum, ethyl cellulose or combinations of the previously mentioned four substances; the non-confined fragrance substance, the entrapped fragrance oil and the suspension agent being premixed prior to the subsequent creation of the liquid or solid fabric softener compositions of matter.

Water soluble polymers have also been used to encapsulate fragrance oils. Such capsules have proved useful in releasing perfume in deodorants. However, such capsules have not been commercially successful in extended release of perfume from fabrics. U.S. Pat. No. 5,425,887 discloses an encapsulated perfume system in tumble dryer articles. The encapsulating material is a water-soluble natural or synthetic polymer with a molecular weight of less than about 300,000 that will release the perfume in response to moisture. Since these systems are water sensitive, these types of particles cannot be incorporated in aqueous fabric softener compositions.

U.S. Pat. Nos. 5,066,419, and 5,154,842 disclose coated perfume particles. The perfume particles comprise perfume dispersed within certain water-insoluble non-polymeric carrier materials and encapsulated in a protective shell by coating with a friable coating material. The coated particles allow for preservation and protection of perfumes, which are susceptible to degradation or loss in storage and in cleaning compositions. In use, the surface coating fractures and the underlying carrier/perfume particles efficiently deliver a large variety of perfume types to fabrics or other surfaces.

Several patents disclose the use of controlled release systems based on cyclodextrin complexes for fabric care applications, for example U.S. Pat. Nos. 5,094,761, 5,207,33, 5,232,612, 5,234,611, 5,236,615, 5,102,564, and 5,234,610. These patents disclose that fabric softening compositions, preferably in liquid form, for use in the rinse cycle of home laundry operations are improved by: (a) using certain protected water sensitive materials, especially particulate complexes of cyclodextrins and perfumes, which are protected in fabric softening compositions and/or detergent compositions, by imbedding the particulate complex in relatively high melting protective material that is substantially water-insoluble and, preferably, non-water-swellable and is solid at normal storage conditions, but which melts at the temperatures encountered in automatic fabric dryers (laundry dryers); (b) using soil release polymers to help suspend water-insoluble particles in aqueous fabric softening compositions; and/or (c) preparing the said protected particulate water sensitive materials (complexes) by melting the said high melting materials, dispersing the said particulate complexes, or other water sensitive material, in the molten high melting protective material and dispersing the resulting molten mixture in aqueous media, especially surfactant solution or aqueous fabric softener composition, and cooling to form small, smooth, spherical particles of the particulate complexes, or other water sensitive material, substantially protected by the high melting material. These systems have the disadvantage that the materials are expensive resulting in increased manufacturing costs.

U.S. Pat. Nos. 4,973,422, and 5,137,646 disclose perfume particles for use in cleaning and conditioning compositions. Perfume particles are disclosed comprising perfume dispersed within wax materials. The particles can be further be coated with a material that makes the particles more substantive to the surface being treated for example, fabric in the laundry process. Such materials help to deliver the particles to the fabric and maximize perfume release directly on the fabric. Generally, the coating materials are water-insoluble cationic materials. Cleaning and conditioning compositions comprising these perfume particles are also disclosed.

U.S. Pat. No. 6,024,943 discloses particles containing absorbed liquids and methods of making them. Perfume is absorbed within organic polymer particles, which have a further polymer at their exterior. The polymer incorporates free hydroxyl groups and serves to promote deposition of the particles from a wash or rinse liquor. The polymer may be part of an encapsulating shell, but more conveniently is used as a stabilizer during polymerization of the particles. Highly hydrolyzed polyvinyl alcohol is preferred. Particles containing organic polymer, which are insoluble in water, with liquid imbibed by the particles, the particles having at their exterior, a polymer which incorporates free hydroxy groups.

U.S. Pat. No. 5,476,660 discloses compositions to deposit an active substance on a target surface. The active substance is left on the surface after the product is rinsed off the surface. The preferred deposition is from compositions containing an anionic or nonionic active in the co-presence of an anionic surfactant. The compositions contain carrier particles having a zwitterionic or cationic surface and a plurality of outwardly protruding filaments containing charged organocarbyl groups. The term "zwitterionic" employed in this patent means a mixture of cationic and anionic (not necessarily neutral); thus the surface of the zwitterionic particles, have both cationic and anionic groups (i.e., positively charged and negatively charged organocarbyl groups). The active substance is contained within the carrier particles. Examples of target surfaces are mammalian skin, hair or nails.

U.S. Pat. No. 6,051,540 discloses a method employing drum chilling for production fragrance-containing long lasting solid particle for incorporation into laundry detergents, fabric softener compositions, and drier-added fabric softener articles. The invention relates to encapsulating a pre-selected fragrance in a fat and a solid, non-ionic, surface active agent, from the group consisting of SPAN® surfactants for the purpose of imparting a fragrance to a laundry detergent composition, a fabric softener composition or a drier-added fabric softener. The invention also relates to a method of formulating a pre-selected fragrance formulation and a fat and surface-active agent carrier for the pre-selected fragrance formulation. The emphasis of U.S. Pat. No. 6,051,540 is in engineering the fragrance formulation and thus limiting the type of fragrances that can be used with the system. This patent also has the drawback that production of these particles, consists of a two step process (i.e., drum chilling and grind) which makes the production of this fragrance-particles to have high manufacturing costs.

U.S. Pat. No. 6,083,899 discloses fabric softener compositions that have enhanced softening benefits. The fabric softeners of consist of a fabric softener active in combination with a cationic charge booster. The cationic charge boosters disclosed are suitable for use with any fabric softener active, preferably with diester and diamide quaternary ammonium (DEQA) compounds. The invention only relates to the enhanced performance of the fabric softener actives as a result of incorporating the cationic charge boosters in these compositions. The invention does not disclose the use of cationic charge booster to deposit particles onto fabric.

It is desirable to provide a controlled delivery systems for fabric care products by maximizing the deposition of the system comprising the active ingredients onto the fabric. The key to maximizing deposition of the system, the nanospheres of this invention, is optimizing particle size to ensure entrainment of the particles within the fabric fibers and having a sufficiently high cationic charge density on the particle surface to maximize ionic interaction between the particles and the fabric. There remains a need in the art for an efficient controlled delivery system, to effectively deposit active ingredients, as well as fragrances, onto fabric and for a method to "boost" the overall charge density of particles thereby providing enhanced deposition onto fabric.

The prior art of which applicant is aware does not set forth a fragrance controlled release system that can be incorporated in a fabric care products to enhance deposition of active ingredients, as well as fragrances, especially not for fragrance ingredients that are more soluble into the aqueous phase of the washing compositions and do not deposit onto the fabric. There is also a need for a fragrance carrier system, for fabric care products, that will allow using a wider range of fragrance ingredients that are currently not substantive on fabric and improved fragrance substantivity and longevity onto the laundered fabric. It is desirable to provide a control release system for overcoming these limitations. It is also desirable to provide a method using an efficient and economical process for effectively delivering a broad range of fragrance ingredients onto fabric and prolong fragrance release from the dry laundered fabric over an extended period of time, or yields a high impact fragrance "burst" upon ironing the fabric.

SUMMARY OF THE INVENTION

The present invention relates to an improved carrier system for fabric care products, such as powder laundry detergents, tumble dryer sheets, and other fabric care products, comprising a plurality of positively charged hydrophobic nano-spheres encapsulated in a water sensitive micro-sphere. A fragrance and active ingredients can be incorporated in the nano-sphere matrix, in the micro-sphere matrix, or in both the nano and micro-spheres matrices. The nano-sphere surface can have a high cationic charge density that improves fragrance deposition onto the laundered fabric. The high cationic charge density on the nano-sphere surface is created by incorporating a cationic fabric conditioning agent into the hydrophobic matrix of the nano-spheres, by incorporating a cationic charge "booster" in the water sensitive micro-sphere matrix, or by using a cationic fabric conditioning agent in the nano-sphere matrix in conjunction with a cationic charge "booster" in the micro-sphere matrix. The fragrance carrier system also provides controlled release or prolonged fragrance release from the dry laundered fabric over an extended period of time, or yields a high impact fragrance "burst" upon ironing the fabric.

In one embodiment, the present invention provides an improved fragrance carrier system for fabric care products, that has improved fragrance substantivity onto clothes which have been laundered and/or which have been treated with fabric softeners and/or which have been treated with rinse added, or drier-added fabric softener products. In the fabric care industry, the term "substantivity" refers to the deposition of the fragrance on the clothes and the retention and perception of the fragrance on the laundered clothing and on the clothing treated with fabric care product. The cationic surface-active agents comprising the fragrance carrier system of the present invention allow a wide range of fragrances and fragrance ingredients to be compatible within the carrier composition and increase the substantivity of fragrances and fragrance ingredients that are currently not substantive on fabric. The fragrance-carrier system also provides prolonged fragrance release from the dry laundered fabric over an extended period of time, or yields a high impact fragrance "burst" upon ironing the fabric. A "fragrance burst" refers to immediate release of the fragrance. In addition, the production of the fragrance-carrier system utilizes minimum processing steps and is efficient and economical.

The carrier system of the present invention is a free-flowing, powder formed of solid hydrophobic positively charged nano-spheres comprising various active ingredients, as well as fragrances, that are encapsulated in a moisture sensitive micro-spheres, characterized by:

(i) protection of the active ingredients, as well as the volatile constituents of the fragrance, during storage, until needed;

(ii) moisture triggered release of the nano-spheres comprising the active ingredients, as well as the fragrance, in response to moisture (upon wash, in the dryer, etc.), and, (iii) enhanced fragrance deposition onto fabric; and (iv) prolonged fragrance release from the dry laundered fabric over an extended period of time; or (v) yield high impact fragrance "burst" upon ironing the fabric.

The invention also provides a method for producing the multi component controlled release system of the present invention including active ingredients that comprise the steps of:

(i) incorporating cationic fabric conditioning agent, active ingredients, and a fragrance into a solid hydrophobic nano-spheres; and (ii) forming an aqueous mixture comprising of one or more active agents, the nano-spheres, a cationic charge booster, and a water sensitive material, such as, starch derivatives, natural gums, polyvinyl alcohol, proteins, hydrocolloids, or mixture of thereof, and (iii) spray drying the mixture to form a dry powder composition.

The invention further provides a process for producing the multi component controlled release system including the active ingredients and the fragrance that comprise the steps of:

(i) heating hydrophobic materials to a temperature above the melting point of the materials to form a melt;

(ii) dissolving or dispersing a cationic fabric conditioning agent into the melt;

(iii) dissolving or dispersing the fragrance and a first active agent into the melt;

(iv) dissolving or dispersing a second active agent, a cationic charge booster, and moisture sensitive materials, such as, starch derivatives, natural gums, polyvinyl alcohol, proteins, hydrocolloids, or mixture of thereof, in the aqueous phase;

(v) heating the composition to above the melting temperature of the hydrophobic material;

(vi) mixing the hot melt with the aqueous phase to form a dispersion;

(vii) high shear homogenization of the dispersion at a temperature above the melting temperature until a homogeneous fine dispersion is obtained having a sphere size of from about 1 micron to about 2 microns;

(viii) cooling the dispersion to ambient temperature; and (ix) spray drying the emulsified mixed suspension to form a dry powder composition The incorporation of spray dried nano-spheres comprising fragrances and other active agents encapsulated within a moisture sensitive matrix in fabric care products was found to enhance fragrance deposition onto fabric, and to extend the release rate of these fragrances and other active ingredients over an extended period of time. In an alternate embodiment, a controlled release composition is formed of hydrophobic nano-spheres incorporating active agents.

The invention also provides a fabric care product such as fabric softener, powder laundry detergents, tumble dryer sheets, and other fabric care products, comprising the multi component controlled release system of the present invention. Fabric laundered with powder laundry detergent or tumble dryer sheets comprising the multi component controlled release system of the present invention were observed to exhibit high level of fragrance (high odor intensity) in both the wet and the dry state and fragrance perception on the dry laundered fabric has been observed to be perceived over an extended period of time, i.e., two to three weeks.

The present invention addresses the foregoing need to increase the deposition of wide range of fragrances and fragrance ingredients onto fabric and prolong their release so that the laundered fabric remains aesthetically pleasing for an extended period of time by employing an advanced carrier system to bring the fragrance onto the clothes.

It is believed that the cationic charge groups on the nano-sphere surface become associated, in use of the composition, with the fabric and assists in adhering the nano-spheres onto fabric during the washing cycle through both sphere entrainment and electrostatic interactions to effectively deliver fragrance onto fabric and sustain fragrance release rate. The hydrophobic matrix sustains the diffusion rate of the fragrance through the nano-spheres and enables the fragrance to be released from the dry laundered fabric over an extended period of time, or during heat treatment such as ironing.

The multi-component controlled release system of the present invention can comprise from about 1% to about 50% by weight hydrophobic matrix, from about 1% to about 50% by weight water sensitive matrix, from about 0% to about 10% by weight cationic charge booster, from about 0.01% to about 10% by weight cationic fabric softening agents, and from about 1% to about 50% by weight fragrance. The micro-sphere have an average sphere size in the range from about 20 microns to about 100 microns, the nano-sphere have an average sphere size in the range from about 0.01 micron to about 5 microns and having a melting point in the range from about 30 degrees C. to about 100 degrees C. The micro-spheres can be incorporated into any fabric care products, preferably in powder laundry detergent, fabric softener, or tumble dryer sheet compositions.

The carrier system of the present invention can be incorporated in tumble-dryer sheets as well as dry granular or powder fabric care compositions and provide long-term storage stability.

DETAILED DESCRIPTION

Figure 1:
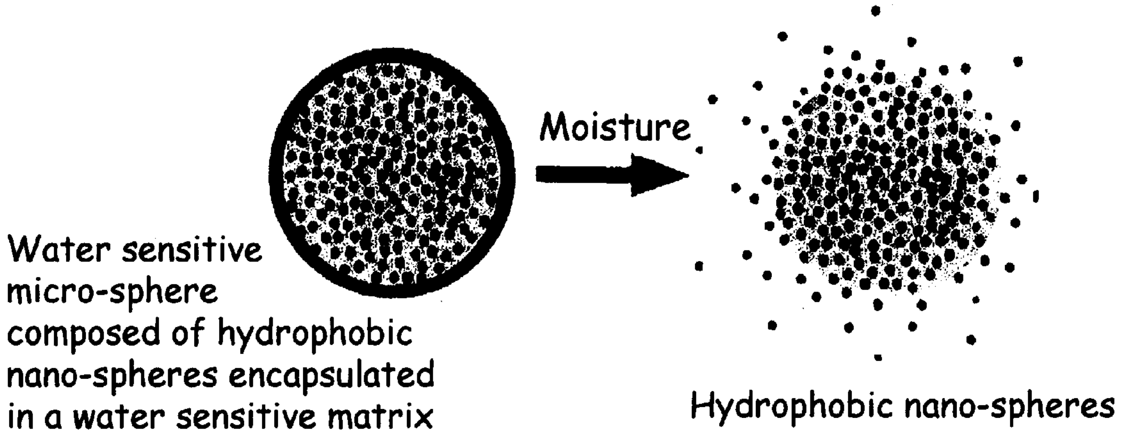
FIG. 1 is a schematic diagram of the controlled release system of the present invention.

The present invention features a method of controlling the release rate of an active agent, as well as fragrances, that can be incorporated in a fabric care product, and provide fragrance release over an extended period of time, or yield a high impact fragrance "burst" upon ironing. The carrier system of the present invention is a free-flowing powder formed of solid hydrophobic, positively charged, nano-spheres comprising active ingredients, as well as fragrances, that are encapsulated in a moisture sensitive micro-sphere, as shown in FIG. 1. The high cationic charge density on the nano-sphere surface improves fragrance deposition onto the laundered fabric. The high cationic charge density on the nano-sphere surface is created by incorporating a cationic fabric conditioning agent into the solid hydrophobic matrix of the nano-spheres, by incorporating a cationic charge "booster" in the water sensitive micro-sphere matrix, or by using a cationic fabric conditioning agent in the nano-sphere matrix in conjunction with a cationic charge "booster" in the micro-sphere matrix. The term "spheres" is intended to describe solid, substantially spherical particulates. It will be appreciated that other sphere shapes can be formed in accordance with the teachings of the present invention.

The nano-spheres of the present invention have an average diameter in the range from about 0.01 micron to about 10 microns. Preferably, the sphere size of the nano-spheres is in the range from about 0.05 microns to about 2 microns. It has been found that spheres within the range of about 0.5 microns to about 1 micron are efficiently entrained on fabric surfaces and are not noticeable on the fabrics. This linear dimension for any individual sphere represents the length of the longest straight line joining two points on the surface of the sphere.

Additional components or agents can be added to the fragrance carrier system or can be incorporated into either the nano or micro-sphere matrices. For example, additional components or agents that can be included in the fragrance carrier system are: ironing aids such as silicones; anti-shrinkage agents; anti-wrinkle agents; bleaching agents, fabric crisping agents; spotting agents; germicides; fungicides; stabilizers preservatives; bactericides which can be effective to protect the composition or to treat fabrics; flow agents; and mixtures thereof. The additional components can be present in an amount from about 1% to about 20% by weight of the spheres.

I. Cationic Charge Boosters

The fragrance carrier system of the present invention may comprise a cationic charge booster to enhance the cationic charge density on the nano-sphere surface. Suitable cationic charge boosters are described in U.S. Pat. No. 6,083,899 hereby incorporated by reference into this application. Suitable examples of cationic charge boosters of the present invention are described herein below.

I.a. Quaternary Ammonium Compounds

A preferred composition of the present invention comprises at least about 0.1%, preferably from about 0.1% to about 10%, more preferably from about 0.1% to about 5% by weight, of a cationic charge booster having the formula:

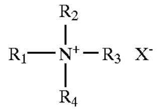

wherein $R_1$, $R_2$, $R_3$, and $R_4$ are each independently $C_1$–$C_{22}$ alkyl, $C_3$–$C_{22}$ alkenyl, $R_5$ —Q—$(CH_2)_m$—, wherein $R_5$ is $C_1$–$C_{22}$ alkyl, and mixtures thereof, m is from 1 to about 6; X is an anion. Preferably $R_1$ is $C_6$–$C_{22}$ alkyl, $C_6$–$C_{22}$ alkenyl, and mixtures thereof, more preferably $R_1$ $C_{11}$–$C_{18}$ alkyl, $C_{11}$–$C_{18}$ alkenyl, and mixtures thereof, $R_2$, $R_3$, and $R_4$ are each preferably $C_1$–$C_4$ alkyl, more preferably each $R_2$, $R_3$, and $R_4$ are methyl.

Alternatively, $R_1$ can be a $R_5$ —Q—$(CH_2)_m$— moiety wherein $R_5$ is an alkyl or alkenyl moiety having from 1 to 22 carbon atoms, preferably the alkyl or alkenyl moiety when taken together with the Q unit is an acyl unit. For example Q can be derived from a source of triglyceride selected from tallow, partially hydrogenated tallow, lard, partially hydrogenated lard, vegetable oils, partially hydrogenated vegetable oils, such as canola oil, safflower oil, peanut oil, sunflower oil, corn oil, soybean oil, tall oil, rice bran oil, and the like and mixtures thereof.

An example of a fabric softener cationic booster comprising a $R_5$ —Q—$(CH_2)_m$— moiety has the formula:

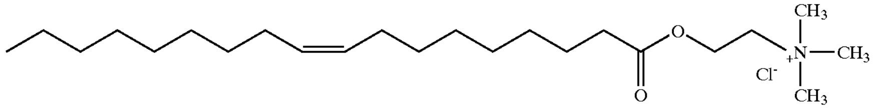

wherein $R_5$ —Q—represents oleoyl units and m is equal to 2.

Preferably X is a softener compatible anion, such as the anion of a strong acid. For example, X can be chloride, bromide, methylsulfate, ethylsulfate, sulfate, nitrate and mixtures thereof. More preferably X is chloride and methyl sulfate.

I.b. Polyvinyl Amines

A preferred composition according to the present invention contains at least about 0.1%, preferably from about 0.1% to about 10%, more preferably from about 0.1% to about 5% by weight, of one or more polyvinyl amines charge boosters having the formula

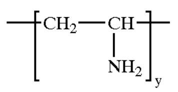

wherein y is from about 3 to about 10,000, preferably from about 10 to about 5,000, more preferably from about 20 to about 500. Polyvinyl amines suitable for use in the present invention are available from BASF under the name Lupasol® LU 321. The greater number of amine moieties per unit weight on the polyvinyl amines provides preferred substantial charge density.

I.c. Polyalkyleneimines

A preferred composition of the present invention comprises at least about 0.1%, preferably from about 0.1% to about 10%, more preferably from about 0.1% to about 5% by weight, of a polyalkyleneimine charge booster having the formula:

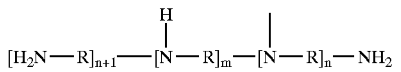

wherein the value of m is from 2 to about 700 and the value of n is from 0 to about 350. Preferably the compounds of the present invention comprise polyamines having a ratio of m:n that is at least 1:1 but may include linear polymers (n equal to 0) as well as a range as high as 10:1, preferably the ratio is 2:1. When the ratio of m:n is 2:1, the ratio of primary-:secondary:tertary amine moieties of $—RNH_2$,—RNH, and —RN moieties, is 1:2:1. R can be $C_2$–$C_8$ alkylene, $C_3$–$C_8$ alkyl substituted alkylene, and mixtures thereof. Preferably R is ethylene, 1,2-propylene, 1,3-propylene, and mixtures thereof, and more preferably ethylene. R radicals serve to connect the amine nitrogens of the backbone.

Optionally, one or more of the polyvinyl amine backbone $—NH_2$ unit hydrogens can be substituted by an alkyleneoxy unit having the formula:

$$—(R_1O)_xR_2$$

wherein $R_1$ is $C_2$–$C_4$ alkylene; $R_2$ is hydrogen, $C_1$–$C_4$ alkyl, and mixtures thereof; and x is from 1 to 50. In one embodiment or the present invention the polyvinyl amine is reacted first with a substrate which places a 2-propyleneoxy unit directly on the nitrogen followed by reaction of one or more moles of ethylene oxide to form a unit having the general formula:

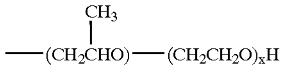

wherein x has the value of from 1 to about 50. Substitutions such as the above are represented by the abbreviated formula PO—$EO_x$—. However, more than one propyleneoxy unit can be incorporated into the alkyleneoxy substituent.

The preferred polyamine cationic charge boosters of the present invention comprise backbones wherein less than about 50% of the R groups comprise more than 3 carbon atoms. The use of two and three carbon spacers as R moieties between nitrogen atoms in the backbone is advantageous for controlling the charge booster properties of the molecules. More preferred embodiments of the present invention comprise less than about 25% moieties having more than 3 carbon atoms. Yet more preferred backbones comprise less than about 10% moieties having more than 3 carbon atoms. Most preferred backbones comprise about 1100% ethylene moieties.

The cationic charge boosting polyamines of the present invention can comprise homogeneous or non-homogeneous polyamine backbones, preferably homogeneous backbones. For the purpose of the present invention the term "homogeneous polyamine backbone" is defined as a polyamine backbone having R units that are the same such as, all ethylene. However, this definition does not exclude polyamines that comprise other extraneous units comprising the polymer backbone that are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention.

For the purposes of the present invention the term "non-homogeneous polymer backbone" refers to polyamine backbones that are a composite of one or more alkylene or substituted alkylene moieties, for example, ethylene and 1,2-propylene units taken together as R units.

Other polyamines that comprise the backbone of the compounds of the present invention are generally polyalkyleneamines (PAA's), polyalkyleneimines (PAI's), preferably polyethyleneamine (PEA's), or polyethyleneimines (PEI's). Polyethyleneimines suitable for use in the present invention are available from BASF under the trade name Lupasol® such as Lupasol™ PR8515, having an average molecular weight of 1,800. A common polyalkyleneamine (PAA) is tetrabutylenepentamine. PEA's can be obtained by reactions involving ammonia and ethylene dichloride, followed by fractional distillation. The common PEA's obtained are triethylenetetramine (TETA) and tetraethylenepentamine (TEPA). Above the pentamines, such as, the hexamines, heptamines, octamines and possibly nonamines, the cogenerically derived mixture does not appear to separate by distillation and can include other materials such as cyclic amines and particularly piperazines.

I.d. Poly-Quaternary Ammonium Compounds

A preferred composition of the present invention comprises at least about 0.1%, preferably from about 0.1% to about 10%, more preferably from about 0.1% to about 5% by weight, of a cationic charge booster having the formula:

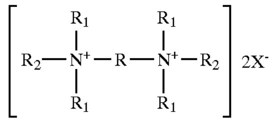

wherein R is substituted or unsubstituted $C_2$–$C_{12}$ alkylene, substituted or unsubstituted $C_2$–$C_{12}$ hydroxyalkylene; each $R_1$ is independently $C_1$–$C_4$ alkyl, each $R_2$ is independently $C_1$–$C_{22}$ alkyl, $C_3$–$C_{22}$ alkenyl, $R_5$ —Q—$(CH_2)_m$—, wherein $R_5$ is $C_1$–$C_{22}$ alkyl, $C_3$–$C_{22}$ alkenyl, and mixtures thereof; m is from 1 to about 6; Q is a carbonyl unit as described above and mixtures thereof; X is an anion.

Preferably R is ethylene and $R_1$ is preferably methyl or ethyl, more preferably methyl. Preferably at least one $R_2$ is $C_1$–$C_4$ alkyl, more preferably methyl. Most preferably at least one $R_2$ is $C_{11}$–$C_{22}$ alkyl, $C_{11}$–$C_{22}$ alkenyl, and mixtures thereof.

Alternatively $R_2$ is a $R_5$ —Q—$(CH_2)_m$— moiety wherein $R_5$ is an alkyl moiety having from 1 to 22 carbon atoms, preferably the alkyl moiety when taken together with the Q unit is an acyl unit derived from a source of triglyceride selected from the group consisting of tallow, partially hydrogenated tallow, lard, partially hydrogenated lard, vegetable oils, partially hydrogenated vegetable oils, such as, canola oil, safflower oil, peanut oil, sunflower oil, corn oil, soybean oil, tall oil, rice bran oil, and the like and mixtures thereof.

An example of a fabric softener cationic booster comprising a $R_5$ —Q—$(CH_2)_m$— moiety has the formula:

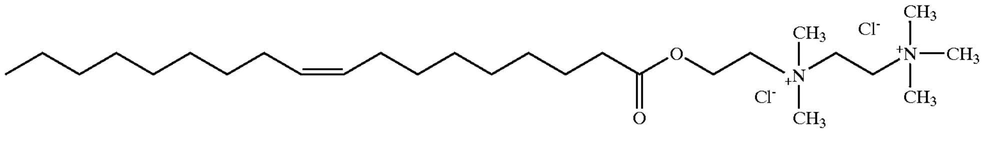

wherein $R_1$ is methyl, one of the $R_2$ units is methyl and the other of the $R_2$ unit is $R_5$ —Q—$(CH_2)_m$— wherein $R_5$ —Q—is an oleoyl unit and m is equal to 2. X is a softener compatible anion, such as an anion of a strong acid. For example, X can be chloride, bromide, methylsulfate, ethylsulfate, sulfate, nitrate and mixtures thereof. More preferably chloride and methyl sulfate.

II. Cationic Fabric Conditioning Agents

The nano-spheres of the present invention comprise any of the cationic fabric conditioning agents known in the art.

Hydrocarbon fabric conditioners suitable for use herein are selected from the following classes of compounds:

(i) Cationic quaternary ammonium salts. The counterion is methyl sulfate or any alkyl sulfate or any halide, methyl sulfate being preferred for the dryer-added articles of the invention.

Examples of cationic quaternary ammonium salts include, but are not limited to:

(1) Acyclic quaternary ammonium salts having at least two $C_{8-30}$, preferably $C_{12-22}$ alkyl chains, such as: ditallowdimethyl ammonium methylsulfate, di(hydrogenated tallow)dimethyl ammonium methylsulfate, distearyldimethyl ammonium methylsulfate, dicocodimethyl ammonium methylsulfate and the like;

(2) Cyclic quaternary ammonium salts of the imidazolinium type such as di(hydrogenated tallow)dimethyl imidazolinium methylsulfate, 1-ethylene-bis(2-tallow-1-methyl) imidazolinium methylsulfate and the like;

(3) Diamido quaternary ammonium salts such as: methyl-bis(hydrogenated tallow amidoethyl)-2-hydroxyethyl ammonium methyl sulfate, methyl bis (tallowamidoethyl)-2-hydroxypropyl ammonium methylsulfate and the like;

(4) Biodegradable quaternary ammonium salts such as N,N-di tallowoyl-oxy-ethyl)-N,N,-dimethyl ammonium methyl sulfate and N,N-di (tallowoyl-oxy-propyl)-N,N-dimethyl ammonium methyl sulfate. Biodegradable quaternary ammonium salts are described, for example, in U.S. Pat. Nos. 4,137,180, 4,767,547 and 4,789,491 incorporated herein by reference.

Preferred biodegradable quaternary ammonium salts include the biodegradable cationic diester compounds (See U.S. Pat. No. 4,137,180, incorporated herein by reference).

(ii) Tertiary fatty amines having at least one and preferably two $C_8$ to $C_{30}$, preferably $C_{12}$ to $C_{22}$ alkyl chains. Examples include hardened tallow-di-methylamine and cyclic amines such as 1-(hydrogenated tallow) amidoethyl-2-(hydrogenated tallow)imidazoline. Cyclic amines which may be employed for the compositions herein are described in U.S. Pat. No. 4,806,255 incorporated herein by reference.

(iii) Carboxylic acids having 8 to 30 carbons atoms and one carboxylic group per molecule. The alkyl portion has 8 to 30, preferably 12 to 22 carbon atoms. The alkyl portion may be linear or branched, saturated or unsaturated, with linear saturated alkyl preferred. Stearic acid is a preferred fatty acid for use in the composition herein. Examples of these carboxylic acids are commercial grades of stearic acid and palmitic acid, and mixtures thereof which may contain small amounts of other acids.

(iv) Esters of polyhydric alcohols such as sorbitan esters or glycerol stearate. Sorbitan esters are the condensation products of sorbitol or iso-sorbitol with fatty acids such as stearic acid. Preferred sorbitan esters are monoalkyl. A common example of sorbitan ester is SPAN 60 (ICI) which is a mixture of sorbitan and isosorbide stearates.

(v) Fatty alcohols, ethoxylated fatty alcohols, alkylphenols, ethoxylated alkylphenols, ethoxylated fatty amines, ethoxylated monoglycerides and ethoxylated diglycerides.

(vi) Mineral oils, and polyols such as polyethylene glycol.

(vii) Silicone oils and silicone surfactants as described in U.S. Pat. No. 5,174,911, incorporated herein by reference.

Suitable softeners are described in U.S. Pat. No. 4,134,838 the disclosure of which is incorporated by reference herein.

Other quaternary ammonium salt fabric conditioning compounds suitable for use in the present invention are described in U.S. Pat. Nos. 3,686,025 and 6,083,899 are described in "Cationic Surfactants", Surfactant Science series, Vol. 34, edited by Richmond J. M., Marcel Dekker Inc., 1990, which are incorporated herein by reference.

The particularly preferred cationic fabric conditioning agents for use in the present invention are: behenyltrimethylammonium chloride; ditallowdimethylammonium methylsulfate; ditallowdimethylammonium chloride; methyl(1) stearylamidoethyl(2)stearylimidazolinium methosulfate; methyl(1)stearylamidoethyl(2)stearylimidazolinium chloride; N,N-di(tallowyl-oxy-ethyl)-N,N-dimethyl ammonium chloride; N,N-di(canolyl-oxy-ethyl)-N,N-dimethyl ammonium chloride; N,N-di(tallowyl-oxy-ethyl)-N-methyl, N-(2-hydroxyethyl) ammonium chloride; N,N-di(canolyl-oxy-ethyl)-N-methyl, N-(2-hydroxyethyl) ammonium chloride; N,N-di(2-tallowyloxy-2-oxo-ethyl)-N,N-dimethyl ammonium chloride; N,N-di(2-canolyloxy-2-oxo-ethyl)-N,N-dimethyl ammonium chloride; N,N-di(2-tallowyloxyethylcarbonyloxyethyl)-N,N-dimethyl ammonium chloride; N,N-di(2-canolyloxyethylcarbonyloxyethyl)-N,N-dimethyl ammonium chloride; N-(2-tallowoyloxy-2-ethyl)-N-(2-tallowyloxy-2-oxo-ethyl)-N,N-dimethyl ammonium chloride; N-(2-canolyloxy-2-ethyl)-N-(2-canolyloxy-2-oxo-ethyl)-N,N-dimethyl ammonium chloride; N,N,N-tri (tallowyl-oxy-ethyl)-N-methyl ammonium chloride; N,N,N-tricanolyl-oxy-ethyl)-N-methyl ammonium chloride; N-(2-tallowyloxy-2-oxoethyl)-N-(tallowyl)-N,N-dimethyl ammonium chloride; N-(2-canolyloxy-2-oxoethyl)-N-(canolyl)-N,N-dimethyl ammonium chloride; 1,2-ditallowyloxy-3-N,N,N-trimethylammoniopropane chloride; and 1,2-dicanolyloxy-3-N,N,N-trimethylammoniopropane chloride; and mixtures of thereof.

Methyl-1-tallowamidoethyl-2-tallowimidazolinium methylsulfate available from Witco Chemical Company under the name Varisoft™ 475. Examples of monoalkyltrimethylammonium salts are monotallowtrimethylammonium chloride, mono(hydrogenated tallow)trimethylammonium chloride, palmityltrimethyl ammonium chloride and soyatrimethylammonium chloride, available from Witco Chemical Company under the names Adogen™ 471, Adogen™ 441, Adogen™ 444, and Adogen™ 415, respectively. Examples of behenyltrimethylammonium chloride are commercially available under the name Kemamine™ Q2803-C from Humko Chemical Division of Witco Chemical Corporation. Methylbis(tallowamidoethyl)(2-hydroxyethyl) ammonium methylsulfate and methylbis(hydrogenated tallowamidoethyl)(2-hydroxyethyl)ammonium methylsulfate; are available from Witco Chemical Company under the names Varisoft™ 222 and Varisoft™ 110, respectively:

dimethylstearylbenzyl ammonium chloride sold under the names Varisoft™ SDC by Witco Chemical Company and Ammonyx™ 490 by Onyx Chemical Company.

The most preferred quaternary ammonium salt fabric conditioning agents are methyl bis(hydrogenated ditallowamidoethyl) 2 hydroxyethyl ammonium chloride, commercially available from Croda Inc. under the name INCROSOFT® 100; methyl bis(hydrogenated tallow amidoethyl)-2-hydroxyethyl ammonium methyl sulfate, commercially available from the Stepan Company under the name ACCOSOFT® 440-75 DEG; methyl (1) hydrogenated tallow amidoethyl (2) hydrogenated tallow imidazolinium methyl sulfate, commercially available from the Stepan Company under the name ACCOSOFT® 808 HT; behenyltrimethylammonium chloride, commercially available under the trade name Kemamine™ Q2803-C from Humko Chemical Division of Witco Chemical Corporation.

III. Matrix Materials for Forming the Nano-Spheres

Suitable solid core materials for forming the nano-spheres of the present invention are inert nontoxic hydrophobic materials with a melting point range between about 30 degrees C. and about 90 degrees C. Examples of hydrophobic materials include natural, regenerated, or synthetic waxes including animal waxes such as beeswax, lanolin and shellac wax, vegetable waxes such as carnauba, candelilla, sugar cane, rice bran, and bayberry wax, mineral waxes such as petroleum waxes including paraffin and microcrystalline wax, and mixtures thereof. Other hydrophobic materials which can be used in the present invention include wax and silicon copolymers, such as candelilla wax and silicone copolymer, ozokrite wax and silicon copolymers, beeswax and silicon copolymers, and the like. Other hydrophobic compounds which can be used in the present invention include: fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol, solid hydrogenated castor and vegetable oils, hard paraffins, hard fats, and mixtures thereof. Other hydrophobic compounds which can be used, include triglycerides, preferably of at least food grade purity, which can be produced by synthesis or by isolation from natural sources. Natural sources can include animal fat or vegetable oil, such as soy oil, as a source of long chain triglycerides (LCT). Other triglycerides suitable for use in the present invention are composed of a majority of medium length fatty acids (C10–C18), denoted medium chain triglycerides (MCT). The fatty acid moieties of such triglycerides can be unsaturated or polyunsaturated and mixtures of triglycerides having various fatty acid material. The nano-sphere matrix can comprise a single hydrophobic material or a mixture of a plurality of materials. Other hydrophobic materials that are known to those skilled in the art and suitable materials as described in "Industrial Waxes," Vol. I and II, by Bennett F.A.I.C., published by Chemical Publishing Company Inc., 1975 and Martindale, "The Extra Pharmacopoeia", The Pharmaceutical Press, $28^{th}$ Edition pp. 1063–1072, 1982 can be used in the present invention.

Other hydrophobic compounds which can be used in the present invention include synthetic polymers, such as alkylated polyvinylpyrrolidines, the Ganex® copolymer series, commercially available from the ISP Company. Examples of other suitable hydrophobic polymers and copolymer for use as the matrix material include polyethylene homopolymers A–C® 1702; A–C® 617, A–C® 617A, and A–C® 15, commercially available from Allied Signal Inc.; PERFORMALENE™ PL available from Baker Pertolite Co.; polyethylene homopolymer commercially available from New Phase Technologies; ETHYLENE-ACRYLIC ACID COPOLYMERS A–C® 540, A–C® 540A, and A–C® 580 commercially available from Allied Signal Inc.; polyamides having a molecular weight in the range of from about 6,000 up to about 12,000, for example, MACROMELT™ 6030 manufactured by the Henkel Ag. of Dusseldorf, Germany; VERSALON™ 1135 polyamide polymer available commercially from General Mills, Inc.

It is preferred that the nano-spheres of the present invention have a melting point in the range from about 30 degrees C. to about 90 degrees C., preferably from about 40 degrees C. to about 90 degrees C. The melting point of the spheres is usually a function of the carrier matrix employed. Accordingly, preferred matrix materials have a melting point in the range of about 50 degrees C. to about 80 degrees C., preferably from about 60 degrees C. to about 70 degrees C. It should be understood that it is the melting point of the sphere rather than of the carrier matrix that is important for use of the carrier system of the present invention.

Considerations in the selection of the matrix material include good barrier properties to the active agents and the fragrance ingredients, low toxicity and irritancy, stability, and high loading capacity for the active agents of interest.

IV. Matrix Materials for Forming the Micro-Sphere Matrix

Water-sensitive materials for forming the micro-spheres of the present invention comprises of water soluble and water dispersible synthetic polymers and copolymers, starch derivatives, polysaccharides, hydrocolloids, natural gums, proteins, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

The polyvinyl alcohol useful in the practice of the invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I-XIV of U.S. Pat. No. 5,051,222 issued on Sep. 24, 1991, the specification for which is incorporated by reference herein.

Polyvinyl alcohol useful for practice of the present invention is Mowiol® 3–83, having a molecular weight of about 14,000 Da and degree of hydrolysis of about 83%, Mowiol® 3-98 and a fully hydrolyzed (98%) polyvinyl alcohol having a molecular weight of 16,000 Da commercially available from Gehring-Montgomery, Inc. of Warminister Pa. Other suitable polyvinyl alcohols are: AIRVOL® 205, having a molecular weight of about 15,000–27,000 Da and degree of hydrolysis of about 88%, and VINEX® 1025, having molecular weight of 15,000–27,000 Da degree of hydrolysis of about 99% and commercially available from Air Products & Chemicals, Inc. of Allentown, Pa.; ELVANOL® 51-05, having a molecular weight of about 22,000–26,000 Da and degree of hydrolysis of about 89% and commercially available from the Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. Of Templefields, Harlow, Essex, England CM20 2BH; and GOHSENOL® GL-03 and GOHSENOL® KA-20 commercially available from Nippon Gohsei K.K., The Nippon Synthetic Chemical Industry Co., Ltd., of No. 9–6, Nozaki Cho, Kita-Ku, Osaka, 530 Japan.

Suitable polysaccharides are polysaccharides of the non-sweet, coloidally-soluble types, such as natural gums, for example, gum arabic, starch derivates, dextrinized and hydrolyzed starches, and the like. A suitable polysaccharide is a water dispersible, modified starch commercially available as Capule®, N-Lok®, Hi-Cap™ 100 or Hi-Cap™ 200 commercially available from the National Starch and Chemical Company of Bridgewater, N.J.; Pure-Cote™, commercially available from the Grain Processing Corporation of Muscatine, Iowa. In the preferred embodiment the natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

V. Fragrances

Preferably, a fragrance is included in the carrier system of the present invention. The fragrance that can be encapsulated in the carrier system of the present invention, can be any odoriferous material and can be selected according to the desires of the fragrance creator. In general terms, such fragrance materials are characterized by a vapor pressure below atmospheric pressure at ambient temperatures. The high boiling perfume materials employed herein will most often be solids at ambient temperatures, but also can include high boiling liquids. A wide variety of chemicals are known for perfumery uses, including materials such as aldehydes, ketones, esters, and the like. More commonly, naturally occurring plant and animal oils and exudates comprising complex mixtures of various chemical components are known for use as fragrances, and such materials can be used herein. Fragrances useful for the present invention can be a single aroma chemical, relatively simple in their composition, or can comprise highly sophisticated, complex mixtures of natural and synthetic chemical components, all chosen to provide any desired odor.

Suitable fragrance which can be used in the present invention comprise, for example the high boiling components of woody/earthy bases containing exotic materials such as sandalwood oil, civet, patchouli oil, and the like. The perfumes herein can be of a light, floral fragrance, such as for example, high boiling components of rose extract, violet extract, and the like. The perfumes herein can be formulated to provide desirable fruity odors, such as for example lime, lemon, orange, and the like. The perfume can be any material of appropriate chemical and physical properties which exudes a pleasant or otherwise desirable odor when applied to fabrics. Perfume materials suitable for use in the present invention are described more fully in S. Arctander, Perfume Flavors and Chemicals, Vols. I and II, Aurthor, Montclair, N.J. and the Merck Index, 8th Edition, Merck & Co., Inc. Rahway, N.J., both references being incorporated herein by reference.

VI. Processing Method

VI.A. Nano-Spheres

The encapsulated active ingredients, as well as the fragrance, in the nano-spheres of the present invention can be prepared by the steps of (1) heating hydrophobic materials to a temperature above the melting point to form a melt, (2) dissolving or dispersing the cationic fabric conditioning agent, the fragrance, and first active ingredient in the melt, (4) emulsifying the melt in the aqueous phase; and (5) cooling the dispersion to ambient temper to form a fine suspension.

The fragrance or other active ingredients can be incorporated into the hydrophobic solid nano-spheres. Preferably, about 1% to about 80% of and more preferably about 1% to about 60% by weight of the active agents are used in forming the nano-spheres.

VI.B. Micro-Spheres

The controlled release system of the present invention can be prepared by the steps of (a) incorporating the cationic fabric conditioning agent, the selected fragrance, and other active agents into the hydrophobic interior of the nano-spheres, (b) forming an aqueous mixture comprising one or more active agents, the nano-spheres, the cationic charge booster and a water sensitive material, and (c) spray drying the mixture of the present invention to form a dry powder composition. Accordingly, the nano-spheres can be encapsulated into the micro-sphere structure. One or more of the active agents which can be the same or different than the active agents incorporated in the nano-sphere can be incorporated into the micro-sphere structure.

A process for producing the multi component controlled release system includes the following stages:

(i) heating a hydrophobic material to a temperature above the melting point to form a melt;

(ii) dissolving or dispersing a cationic fabric conditioning agent into the melt;

(iii) dissolving or dispersing the fragrance and the first active agent into the melt;

(iii) dissolving or dispersing a second active agent, a cationic charge booster, and the water sensitive materials, such as, starch derivative, hydrocolloid, natural gums, polyvinyl alcohol, or mixture of thereof, in the aqueous phase and heating it to above the melting temperature of the hydrophobic material;

(iv) mixing the hot melt with the aqueous phase to form an dispersion;

(v) high shear homogenization of the dispersion at a temperature above the melting temperature until a homogeneous fine dispersion is obtained having a sphere size of from about 1 microns to about 2 microns;

(vi) cooling the dispersion to ambient temperature; and (vii) spray drying the emulsified mixed suspension to form a dry powder composition. Homogenization can be accomplished in any suitable fashion with a variety of mixers known in the art such as simple paddle or ribbon mixers although other mixers, such as ribbon or plow blenders, drum agglomerators, and high shear mixers may be used. Suitable equipment for this process include a model Rannie 100 lab homogenizer available from APV Gaulin Inc. Everett, Mass., a rotor stator high shear mixer available from Silverson Machines, of East Long Meadow, Mass., or Scott Processing Equipment Corp. of Sparta, N.J., and other high sear mixers.

The suspension is spray dried to remove the excess water. Spray drying is well known in the art and been used commercially in many applications, including foods where the core material is a flavoring oil and cosmetics where the core material is a fragrance oil. Cf. Balassa, "Microencapsulation in the Food Industry", CRC Critical Review Journal in Food Technology, Jul. 1971, pp 245–265; Barreto, "Spray Dried Perfumes for Specialties, Soap and Chemical Specialties", December 1966; Maleeny, Spray Dried Perfumes, Soap and San Chem, January 1958, pp. 135 et seq.; Flinn and Nack, "Advances in Microencapsulation Techniques", Batelle Technical Review, Vo. 16, No. 2, pp. 2–8 (1967); U.S. Pat. Nos. 5,525,367; and 5,417,153 which are incorporated herein as references.

In the preferred embodiment, the active agent is present at a level from about 0.01% to about 60%, preferably from about 1% to about 50% by weight of the micro-sphere. Example active agents include a fragrance, ironing aids such as silicones; anti-shrinkage agents; anti-wrinkle agents; bleaching agents, fabric crisping agents; spotting agents; germicides; fungicides; stabilizers preservatives; bactericides which can be effective to protect the composition or to treat fabrics; flow agents; and mixtures thereof. In the preferred embodiment, the nano-spheres are generally present in the water sensitive matrix at a level from about 1% to about 80%, preferably from about 1% to about 60% by weight of the matrix material with the balance being the active agents, the cationic fabric conditioning agent, the cationic charge booster, and the water sensitive materials. In the preferred embodiment, the moisture sensitive matrix is generally present at a level from about 1% to about 80%, preferably from about 1% to about 60% by weight of the matrix material with the balance being the active agents, the cationic fabric conditioning agent, the cationic charge booster, and the hydrophobic materials.

In one embodiment micro-spheres are formed by mixing nano-spheres incorporating a selected active agent with polyvinyl alcohol, or compositions of polyvinyl alcohol and polysaccharides, under conditions sufficient to encapsulate the nano-spheres. Preferably mixing a selected active agent with the polyvinyl alcohol, or compositions of polyvinyl alcohol and polysaccharides, until the emulsion is formed and then spray drying the emulsion to thereby form an encapsulated nano-sphere. In the preferred embodiment, the moisture sensitive matrix is formed of a polyvinyl alcohol material at a level from about 1% to about 80%, preferably from about 1% to about 70% by weight of the matrix material with the balance being the amount by weight of active agents and an optimal amount of polysaccharides. In an alternate embodiment, the polyvinyl alcohol is present in the matrix material in an amount of about 1% to about 80% and the weight of the polysaccharides are present in the amount of about 1% to about 80%. In the preferred embodiment, the active agent composition is generally present at a level from about 0.01% to about 80% preferably from about 1% to about 50% by weight of the encapsulated active agent with the balance being the polyvinyl alcohol or polyvinyl alcohol and polysaccharides. Optionally other conventional ingredients known in the art such as preservatives, surfactants, can be used in accordance with the teachings of the present invention. The multi-component spheres of the present invention can have size of from about 0.5 micron to about 300 microns, more preferably from about 1 micron to about 200 microns, most preferably from about 2 microns to about 50 microns. The present invention preferably has minimal active agents on the surface of the spheres, preferably less than 1%.

Polyvinyl alcohol is an excellent barrier material to the permeation of the volatile fragrance ingredients, and as a result the controlled release systems of the present invention do not provide perceptible odor in the dry state. Upon wetting by a sufficient amount of aqueous fluid such as a body fluid, the matrix can either dissolve to provide a burst of the active ingredients, or swell and soften the matrix to slowly release the encapsulated active agents over an extended period of time, depending on the composition of the matrix, such as the ratio of polyvinyl alcohol to other matrix materials. The use of moisture activated spheres which provide varying rates of diffusion are contemplated. For example, the moisture activated spheres may diffuse at any of the rates of the following:

(i) at steady-state or zero-order release rate in which there is a substantially continuous release per unit of time;

(ii) a first-order release rate in which the rate of release declines towards zero with time; and (iii) a delayed release in which the initial rate is slow, but then increases with time.

It has been found that a greater amount of polyvinyl alcohol in the matrix provides slower release rate as compared to a matrix including a lesser amount of polyvinyl alcohol in combination with a polysaccharide. For example, a matrix having about 70% to about 80% polyvinyl alcohol has a slower release rate than a matrix having about 30% to about 40% polysaccharide and about 40% to about 50% polyvinyl alcohol. For example, if a high amount of polyvinyl alcohol is used in the matrix, such as in the range of about 70% to about 80%, the matrix provides controlled release of the active agent over an extended period of time from the time the matrix contacts moisture up to forty-eight hours. If polyvinyl alcohol is combined with polysaccharide in the matrix, such as in the amount of about 30% to about 40% polyvinyl alcohol and about 30% to about 40% of polysaccharide, a greater amount of active agent is released upon contract with moisture to provide a "burst" of the active agent and the active agent is released over a shorter period of time for example from the time the matrix contacts the fluid up to the range of about 6 hours to about twenty-four hours. Typically, the active agent at the surface of the sphere can be released upon contact with the fluid with the remainder of the active agent being either released in a burst if the matrix dissolves or over an extended period of time upon swelling and softening of the matrix.

Nano-spheres formed of a hydrophobic material provide a controlled release system in order to release the active agent over an extended period of time by molecular diffusion. Active agents in the hydrophobic matrix of the nano-spheres can be released by transient diffusion. The theoretical early and late time approximation of the release rate of the active ingredients dissolved in the hydrophobic matrix of the nano-spheres can be calculated from the following equations:

Early Time Approximation $(m_t/m_{sec})<0.4$ $$\frac{M_t}{M_\infty} = 4\left(\frac{D_p t}{\pi r^2}\right)^{1/2} - \frac{D_p t}{r^2} \tag{1}$$

$$\frac{dM_t/M_\infty}{dt} = 2\left(\frac{D_p}{\pi r^2 t}\right)^{1/2} - \frac{D_p}{r^2} \tag{2}$$

Late Time Approximation $(m_t/m)>0.6$ $$\frac{M_t}{M_\infty}=1-\frac{4}{(2.405)^2}\exp\left(\frac{-(2.405)^2D_pt}{r^2}\right) \quad (3)$$

$$\frac{dM_t/M_\infty}{dt}-1-\frac{4D_p}{r^2}\exp\left(\frac{-(2.405)^2D_pt}{r^2}\right) \quad (4)$$

wherein:

r is the radius of the cylinder, $m_\infty$ is the amount fragrance released from the controlled release system after infinite time;

$m_t$ is the amount fragrance released from the controlled release system after time t; and $D_p$ is the diffusion coefficient of the fragrance or aroma chemical in the matrix The release rate for releasing the fragrance or other active agents from the hydrophobic nano-spheres is typically slower than the release rate for releasing active agent from the moisture sensitive matrix. The active agents can be selected to be incorporated into either the hydrophobic nano-spheres or the moisture sensitive matrix depending on the desired time for release of the active agents. For example, a predetermined first active agent can be incorporated in the moisture sensitive matrix to be released upon wash and a predetermined second active agent can be incorporated in the hydrophobic nano-spheres for release over an extended period of time during or after the first agent has been released. For example, the moisture sensitive matrix formed in accordance with the present invention can release the first active agent upon contact with moisture to provide a "burst" with continued release of the first active agent and nano-spheres formed in accordance with the present invention can release the active agent depending on the release rate from an initial time such as within few days, up to a period of few week.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and claims, are by weight and are approximations unless otherwise stated.

Preparation of the Multi Component Fragrance Delivery System

EXAMPLE 1

The fragrance used in the following examples is a fragrance composition that is not substantive on fabric when used as neat oil. The fragrance composition used is as follows:

| Perfume Composition | Component (% Wt.) |
|---|---|
| Geraniol | 30.0 |
| Dihydro Myrcenol | 25.0 |
| Linalool | 25.0 |
| Tetrahydro Linalyl Acetate | 20.0 |

The following procedure is used for the preparation of multi component controlled release system with a fragrance as the active agent in the hydrophobic nano-sphere matrix. The nano-sphere hydrophobic matrix is candelilla wax, commercially available from Strahl & Pitsch Inc. of West Babylon, New-York, the cationic fabric conditioning agent is methyl bis(hydrogenated ditallowamidoethyl) 2 hydroxyethyl ammonium chloride, commercially available from Croda Inc. as INCROSOFT 100, The micro-sphere water sensitive matrix is Hi-Cap™ 100 (commercially available from the National Starch and Chemical Company of Bridgewater, N.J.).

200 grams of candelilla wax is placed in an oven at 80 degrees ° C. and allowed to melt. 1500 grams of deionized water are placed into 1 gallon vessel, fitted with an all-purpose silicon rubber heater (Cole-Palmer Instrument Company). 450 grams of Hi-Cap™ 100 (commercially available from the National Starch and Chemical Company of Bridgewater, N.J.) was added to the water and the aqueous solution is heated to 90 degree C. while mixing it with a propeller mixer. The candelilla wax is removed from the oven, 50 grams of the cationic fabric conditioning agent, methyl bis(hydrogenated ditallowamidoethyl) 2 hydroxyethyl ammonium chloride, commercially available from Croda Inc. as INCROSOFT 100, and 300 grams of the fragrance are mixed into the melt by hand with a glass rod. The fragrance/conditioning agent/wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 30% fragrance encapsulated in the solid hydrophobic nano-spheres. The multi component controlled release system obtained contains 30% fragrance, 20% candelilla wax, 5% conditioning agent, and 45% water sensitive material.

EXAMPLE 2

The following procedure is used for the preparation of multi component controlled release system with a fragrance as the active agent in the hydrophobic nano-sphere matrix. The nano-sphere hydrophobic matrix is polyethylene homopolymer, commercially available from New Phase Technologies as PERFORMALENE™ PL, the cationic fabric conditioning agent is methyl bis(hydrogenated ditallowamidoethyl) 2 hydroxyethyl ammonium chloride, commercially available from Croda Inc. as INCROSOFT 100. The micro-sphere water sensitive matrix is Hi-Cap™ 100 (commercially available from the National Starch and Chemical Company of Bridgewater, N.J.), the cationic charge booster incorporated in the micro-sphere water sensitive matrix is polyethyleneimine having an average molecular weight of 1800, commercially available from BASF Corporation as LUPASOL™ PR815

200 grams of polyethylene homopolymer is placed in an oven at 90 degrees ° C. and allowed to melt. 1500 grams of deionized water are placed into 1 gallon vessel, fitted with an all-purpose silicon rubber heater (Cole-Palmer Instrument Company). 449 grams of Hi-Cap™ 100 (commercially available from the National Starch and Chemical Company of Bridgewater, N.J.) and 1 gram of polyethyleneimine having an average molecular weight of 1800, commercially available from BASF Corporation as LUPASOL™ PR815 is added to the water and the aqueous solution is heated to 95 degree C. while mixing it with a propeller mixer. The polyethylene homopolymer is removed from the oven, 50 grams of the cationic fabric conditioning agent, methyl bis(hydrogenated ditallowamidoethyl) 2 hydroxyethyl ammonium chloride, commercially available from Croda Inc. as INCROSOFT 100, and 300 grams of the fragrance are mixed into the polymer by hand with a glass rod. The fragrance/conditioning agent/polyethylene polymer mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 30% fragrance encapsulated in the solid hydrophobic nano-spheres. The multi component controlled release system obtained contains 20% hydrophobic polymer, 5% conditioning agent in hydrophobic matrix of the nano-spheres, 44.9% water sensitive material, and 0.1% cationic charge "booster" in the water sensitive matrix of the micro-spheres.

Test Methods

Twenty cotton towels having the following dimensions 14"×17" were used for evaluating the performance of the fragrance carrier spheres of the present invention. Ten of the towels were 100% cotton and ten were composed of a mixture of 65% polyester and 35% cotton. The fabric was laundered in an American washing machine Kenmore™ 90 series.

Wash Conditions:

Fabric Load: 20 towels

Laundry detergent sample size: 100 grams

Fabric softener sample size: 30 grams

Dosing into the machine: Laundry detergent was dosed directly into the machine Fabric softener was placed in the dispenser Water level: Small Load Water temperature: Cold/Cold Cycle: Short cycle Water temperature: Cold/Cold Rinse options: One rinse cycle Speeds: Heavy duty The laundered fabric was line dried overnight in a fragrance free room. The dry fabric was folded into two and placed into an aluminum tray, approximately 5 cm deep, covered with a perforated aluminum sheet, in order to keep it out of view, up to the moment of the sniff-test. The sniff-test was performed on the dry laundered fabric in a "pre-ventilated" room by ten graders, 24 hours following wash. The laundered fabric was then covered with a perforated aluminum sheet, and was evaluated again after one week and two weeks by a sniff-test method.

Odor perception is, by its nature, a very subjective determination. According to the procedure, the samples to be tested are provided to a panel of ten odor specialists who independently rank odor intensity of the dry laundered fabric using a scale of 1 (no perceived odor) to 10 (high odor intensity). Samples yielding an odor ranking below about 2 possess an odor which would hardly be noticed by the general public.

Incorporation of the Multi Component Controlled Release System in Fabric Care Products

EXAMPLE 3

The performance of a powder laundry detergent product comprising the fragrance carrier system of Example 1 (i.e., the ability to increase fragrance deposition onto fabric, as well as the ability to prolong fragrance release from the dry laundered fabric over an extended period of time, or yield a high impact fragrance "burst" upon ironing the fabric) was evaluated and compared to the performance of the same detergent comprising the neat fragrance, at the same fragrance level. The unfragranced powder laundry detergent base was a commercial TIDE™ FREE powder laundry detergent available from Procter & Gamble Company of Cincinnati, Ohio that is fragrance free.

The laundry samples were prepared at a 1% effective fragrance concentration using the fragrance described in Example 1. The control sample was prepared by weighting into a jar 1 gram of the neat fragrance and 99 grams of the TIDE™ FREE unfragranced and the resulting mixture was mixed for about one hour. The powder laundry detergent comprising the fragrance spheres of the present invention was prepared by weighting into a jar 3.3 grams of the fragrance spheres of example 2 and 96.7 grams of the TIDE™ FREE unfragranced powder laundry detergent base and the resulting mixture was mixed for about one hour.

Twenty towels were placed in the washing machine (10 of the towels used were 100% cotton and the other 10 towels were 65% polyester and 35% cotton) with 100 grams of powder laundry detergent dosed directly into the washing machine.

The following washing machine cycle was used:

Fabric Load: 20 towels

Laundry detergent sample size: 100 grams

Dosing into the machine: Laundry detergent was dosed directly into the machine

Water level: Small Load

Water temperature: Cold/Cold

Cycle: Short cycle

Water temperature: Cold/Cold

Rinse options: One rinse cycle

Speeds: Heavy duty

Cloth samples were line-dried for 24 hours and then evaluated at four stages: immediately after drying (24 hours following wash); upon ironing 24 hours following wash; at one week after drying; and at two weeks after drying. The dry fabric was folded into two and placed into an aluminum tray, approximately 5 cm deep, covered with a perforated aluminum sheet, between the evaluation stages, up to the moment of the sniff-test. The sniff-test was performed on the dry laundered fabric in a "pre-ventilated" room by ten graders, and test results are presented below:

| | 24 Hours Following Wash | |
|---|---|---|
| Sample | Dry Fabric | Upon Ironing |
| Neat Fragrance (Control) | 3 | 5 |
| Encapsulated Fragrance (Example 1) | 7 | 8 |

Test results indicate that the cloth samples washed with the encapsulated fragrance of Example 1 are significantly more intense than the control samples washed with the neat fragrance immediately after drying (24 hours following wash).

A significant increase in fragrance intensity was observed upon ironing the fabric laundered with the encapsulated fragrance spheres of Example 1. Although odor intensity of the fabric laundered with the neat fragrance (control) was observed to be directly more intense, upon ironing, no significant increase in odor intensity was observed. Only a slight increase in odor intensity was observed when ironing the fabric laundered with the neat fragrance (control).

| Sample | One Week | Two Weeks |
| --- | --- | --- |
| Neat Fragrance (Control) | 2 | 1 |
| Fragrance Sphere (Example 1) | 6 | 5 |

At week one and week two the test results indicate that the cloth samples washed with the encapsulated fragrance of Example 1 are significantly more intense than the control samples washed with the neat fragrance (control). The products comprising the encapsulated fragrance show significant improvement over the performance of the neat fragrance in sustaining the volatile constituents of the fragrance and providing a prolong fragrance release from the dry laundered fabric over an extended period of time.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed is:

1. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said solid nanoparticles are positively charged, wherein said nano-particles further comprise a cationic fabric conditioning agent.

2. The composition of claim 1 wherein said cationic fabric conditioning agent is quaternary ammonium salt or cationic imidazolinium.

3. The composition of claim 1 wherein said cationic fabric conditioning agent is a dialkyl dimethyl ammonium chloride or alkyl trimethyl ammonium compound wherein the alkyl has from 12 to 20 atoms.

4. The composition of claim 1 wherein said cationic fabric conditioning agent is selected from the group consisting of: behenyltrimethylammonium chloride; ditallowdimethylammonium methylsulfate; ditallowdimethylammonium chloride; methyl(1) stearylamidoethyl (2) stearylimidazolinium methosulfate; methyl(1)stearylamidoethyl(2) stearylimidazolinium chloride; N,N-di(tallowyl-oxy-ethyl)-N,N-dimethyl ammonium chloride; N,N-di(canolyl-oxy-ethyl)-N,N-dimethyl ammonium chloride; N,N-di(tallowyl-oxy-ethyl)-N-methyl, N-(2-hydroxyethyl) ammonium chloride; N,N-di(canolyl-oxy-ethyl)-N-methyl, N-(2-hydroxyethyl) ammonium chloride; N,N-di(2-tallowyloxy-2-oxo-ethyl)-N,N-dimethyl ammonium chloride; N,N-di(2-canolyloxy-2-oxo-ethyl)-N,N-dimethyl ammonium chloride; N,N-di(2-tallowyloxyethylcarbonyloxyethyl)-N,N-dimethyl ammonium chloride; N,N-di(2-canolyloxyethylcarbonyloxyethyl)-N,N-dimethyl ammonium chloride; N-(2-tallowoyloxy-2-ethyl)-N-(2-tallowyloxy-2-oxo-ethyl)-N,N-dimethyl ammonium chloride; N-(2-canolyloxy-2-ethyl)-N-(2-canolyloxy-2-oxo-ethyl-N,N-dimethyl ammonium chloride; N,N,N-tri(tallowyl-oxy-ethyl)-N-methyl ammonium chloride; N,N,N-tricanolyl-oxy-ethyl)-N-methyl ammonium chloride; N-(2-tallowyloxy-2-oxoethyl)-N-(tallowl)-N,N-dimethyl ammonium chloride; N-(2-canolyloxy-2-oxoethyl)-N-(canolyl)-N,N-dimethyl ammonium chloride; 1,2-ditallowyloxy-3-N,N,N-trimethylammoniopropane chloride; and 1,2-dicanolyloxy-3-N,N,N-trimethylammoniopropane chloride; and mixtures of thereof.

5. The composition of claim 1 wherein said cationic fabric conditioning agent comprises methyl bis(hydrogenated ditallowamidoethyl) 2 hydroxyethyl ammonium chloride.

6. The composition of claim 1 wherein said cationic fabric conditioning agent comprises methyl bis(hydrogenated tallow amidoethyl)-2-hydroxyethyl ammonium methyl sulfate.

7. The composition of claim 1 wherein said cationic fabric conditioning agent comprises methyl (1) hydrogenated tallow amidoethyl (2) hydrogenated tallow imidazolinium methyl sulfate.

8. The composition of claim 1 wherein said cationic fabric conditioning agent comprises behenyltrimethylammonium chloride.

9. The composition of claim 1 wherein said micro-spheres further comprise a cationic charge booster selected from the group consisting of a quaternary ammonium compound, polyvinyl amine, polyalkyleneimine, and a poly-quaternary ammonium compound.

10. The composition of claim 9 wherein said nano-spheres release said cationic fabric conditioning agent over an extended period of time.

11. The composition of claim 10 wherein said extended period of time is up to about 3 weeks.

12. The composition of claim 9 wherein said micro-spheres release an effective amount of said cationic charge booster and said nano-spheres release an effective amount of said cationic fabric conditioning agent to provide a burst upon heat treatment of said sphere.

13. A method for producing the composition of claim 9 comprising the steps of:

(i) incorporating the first active agent and said cationic fabric conditioning agent into said nano-spheres;

(ii) forming an aqueous mixture comprising said nano-spheres, said second active agent, and said cationic charge booster and said moisture sensitive material; and (iii) spray drying said mixture to form a dry powder composition.

14. A method for producing the composition of claim 9 comprising the steps of:

(i) heating a hydrophobic material for forming said nano-spheres to a temperature above a melting point of said hydrophobic material to form a melt;

(ii) dissolving or dispersing the cationic fabric conditioning agent into said melt;

(iii) dissolving or dispersing a fragrance and said first active agent into said melt;

(iv) dispersing said second active agent, said cationic charge booster, and said moisture sensitive matrix material in the aqueous phase;

(v) heating the dispersion to above the melting temperature of said hydrophobic material to form a hot melt;

(vi) mixing said hot melt with the aqueous phase to form a dispersion;

(vii) homogenizing the dispersion at a temperature above the melting temperature until a homogeneous fine dispersion is obtained having a particle size of from about 1 micron to about 2 microns;

(viii) cooling the homogenized dispersion to ambient temperature to form a suspension; and (ix) spray drying the emulsified mixed suspension to form a dry powder composition.

15. The composition of claim 1 wherein said moisture sensitive matrix material is selected from the group consisting of a water soluble synthetic polymer, water dispersible synthetic polymers, a starch derivative, natural gum, polyvinyl alcohol, polysaccharide, protein, hydrocolloid, and mixtures thereof.

16. The composition of claim 15 wherein said hydrocolloid is selected from the group consisting of xanthan, maltodextrin, galactomanan, and tragacanth.

17. The composition of claim 15 wherein said starch derivative is present in an amount by weight of about 1% to about 70% by weight of said micro-sphere.

18. A fabric care product comprising said composition of claim 1.

19. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said micro-spheres further comprise a cationic charge booster selected from the group consisting of a quaternary ammonium compound, polyvinyl amine, polyalkyleneimine, and a poly-quaternary ammonium compound, wherein said solid nanoparticles are positively charged.

20. The composition of claim 19 wherein said cationic charge booster comprises polyethyleneimine, having an average molecular weight of 1,800.

21. The composition of claim 19 wherein said cationic charge booster comprises polyethyleneimine, having an average molecular weight of 1,800.

22. A fabric care product comprising said composition of claim 19.

23. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said first active agent is selected from one or more of the agents of the group consisting of a fragrance, ironing aid, silicones, anti-shrinkage agent, anti -wrinkle agent, fabric crisping agent, bleaching agent, spotting agent, germicide, fungicide, stabilizer, preservative, bactericide, flow agent, and mixtures thereof, wherein said solid nanoparticles are positively charged.

24. The composition of claim 23 wherein said first active agent comprises a fragrance.

25. A fabric care product comprising said composition of claim 23.

26. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, a second active agent encapsulated in said moisture sensitive matrix wherein said matrix releases said second active agent upon contact with said moisture and continuously thereafter for an extended period of time, wherein said solid nanoparticles are positively charged.

27. The composition of claim 26 wherein said second active agent is selected from one or more of the agents of the group consisting of a fragrance, ironing aid, silicones, anti-shrinkage agent, anti-wrinkle agent, fabric crisping agent, spotting agent, bleaching agent, germicide, fungicide, stabilizer, preservative, bactericide, flow agent, and mixtures thereof.

28. The composition of claim 27 wherein said second active agent is a fragrance.

29. A fabric care product comprising said composition of claim 26.

30. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material of gum arabic, wherein said solid nanoparticles are positively charged.

31. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material is polyvinyl alcohol, said polyvinyl alcohol is present in an amount by weight of about 1% to about 70% by weight of said particle, wherein said solid nanoparticles are positively charged.

32. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, wherein said moisture sensitive matrix material is polyvinyl alcohol, said polyvinyl alcohol is present in an amount by weight of about 70% to about 80% of said particle, wherein said solid nanoparticles are positively charged.

33. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, wherein said moisture sensitive matrix material is said polyvinyl alcohol, said polyvinyl alcohol has a degree of hydrolysis from about 75% to about 99%, wherein said solid nanoparticles are positively charged.

34. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, wherein said moisture sensitive matrix material is a starch derivative is present in an amount by weight of about 30% to about 40% of said sphere and said polyvinyl alcohol is present in an amount by weight of about 30% to about 40% of said sphere, wherein said nanoparticles are positively charged.

35. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said hydrophobic material is selected from the group consisting of natural waxes and synthetic waxes, natural wax and silicon copolymers, synthetic wax and silicon copolymer, fatty acid esters, fatty alcohols, solid hydrogenated plant oils, natural polymers and synthetic polymers, wherein said solid nanoparticles are positively charged.

36. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said hydrophobic material comprises candelilla wax, wherein said solid nanoparticles are positively charged.

37. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said hydrophobic material comprises candelilla wax and silicon copolymer, wherein said nanoparticles are positively charged.

38. A multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said first active agent comprises about 1% to about 50% by weight of a fragrance, wherein said solid nanoparticles are positively charged.

39. The composition of claim 38 further comprising about 1% to about 10% of an active agent selected from the group consisting of fragrances, ironing aids, silicones, anti-shrinkage agents, anti-wrinkle agents, fabric crisping agents, bleaching agent, spotting agents, germicides, fungicides, stabilizers, preservatives, bactericides, flow agents, and mixtures thereof.

40. A method for providing fragrance control release over an extended period of time in a fabric care product comprising the step of providing a moisture activated composition, comprising a fragrance incorporated into a hydrophobic positively charged nano-particle and encapsulated in a moisture sensitive matrix material.

41. A method for providing fragrance control release over an extended period of time in a fabric care product comprising the step of providing a moisture activated composition, said composition comprising:

a plurality of solid nanoparticles, each of said solid nanoparticles comprising an effective amount of a first active agent, said solid nanoparticles are formed of a hydrophobic material said plurality of nanoparticles being encapsulated in a moisture sensitive microparticle, said moisture sensitive microparticle is formed of a moisture sensitive matrix material, wherein said solid nanoparticles are positively charged.

42. A fabric care product comprising a multi component moisture activated composition comprising:

a plurality of solid nanoparticles, each of said solid nanoparticles comprising an effective amount of a first active agent, said solid nanoparticles are formed of a hydrophobic material, said plurality of nanoparticles being encapsulated in a moisture sensitive microparticle, said moisture sensitive microparticle is formed of a moisture sensitive matrix material, said solid nanoparticles are positively charged wherein said fabric care product is selected from the group consisting of: a fabric softener; tumble dryer sheets, powder laundry detergent; rinse added product; drier-added fabric softener product; and ironing added product.

* * * * *